United States Patent [19]

Biedermann

[11] Patent Number: 5,800,565
[45] Date of Patent: Sep. 1, 1998

[54] LEG PROSTHESIS WITH QUICK EXCHANGE AND DISPLACEMENT ADJUSTMENT CONNECTIONS

[75] Inventor: Lutz Biedermann, VS-Villingen, Germany

[73] Assignee: Biedermann Motech GmbH, VS-Schwenningen, Germany

[21] Appl. No.: 737,018

[22] PCT Filed: Apr. 27, 1995

[86] PCT No.: PCT/EP95/01609

§ 371 Date: Oct. 29, 1996

§ 102(e) Date: Oct. 29, 1996

[87] PCT Pub. No.: WO95/31949

PCT Pub. Date: Nov. 30, 1995

[30] Foreign Application Priority Data

May 25, 1994 [DE] Germany .................. 94 08 556 U

[51] Int. Cl.[6] .................. A61F 2/62; A61F 2/64; A61F 2/76
[52] U.S. Cl. .................. 623/38; 623/27; 623/44
[58] Field of Search .................. 623/38, 39, 43, 623/44, 40–42, 45, 46, 35, 50–52, 27

[56] References Cited

U.S. PATENT DOCUMENTS 3,538,516  11/1970  Bailey .
3,551,915   1/1971  Woodall .
3,671,978   6/1972  May ............................. 623/38
4,536,898   8/1985  Palfray ........................ 623/33
4,883,494  11/1989  Cooper ........................ 623/39
5,047,063   9/1991  Chen .......................... 623/38
5,171,325  12/1992  Aulie ......................... 623/43
5,181,931   1/1993  van de Veen .................. 623/40
5,529,576   6/1996  Lundt et al. .................. 623/38

FOREIGN PATENT DOCUMENTS 0 439 028A2   7/1991  European Pat. Off. .
1502061      11/1967  France ........................ 623/38
2410998       8/1979  France ........................ 623/38
2630642 A1   11/1989  France ........................ 623/39
2 123 814     1/1972  Germany ....................... 623/38
1114312       5/1968  United Kingdom .
2 089 216 A   6/1982  United Kingdom ................ 623/39

*Primary Examiner*—David H. Willse
*Attorney, Agent, or Firm*—George W. Neuner

[57] ABSTRACT

A test prosthesis comprising a thigh member (6), a lower leg member (7), a joint (4) connecting both members and a knee part (1) is provided. The knee part (1) is connected to the thigh member (6) or to the lower leg member (7), respectively, through a connection unit (8) allowing a relative movement of the connected members in a direction inclined with respect to the leg axis. This allows a relative adjustment of the position of the members, whereby a selection of the correct prosthesis for a thigh amputated person is easily possible by testing different members.

12 Claims, 3 Drawing Sheets

LEG PROSTHESIS WITH QUICK EXCHANGE AND DISPLACEMENT ADJUSTMENT CONNECTIONS

The invention relates to a leg prosthesis, in particular, to device in form of a test prosthesis for testing various combinations of the possible members of the prosthesis and their adaptation to the anatomical conditions. A prosthesis for a thigh amputated person, i.e. for a person having the leg amputated above the knee, conventionally comprises a thigh member, a lower leg member with a foot member, a joint and a swing phase control device, whereby the thigh member is pivotally connected to the lower leg member through the joint. The swing phase control device comprises a first link part and a second link part, whereby the first link part is connected to the thigh member and the second link part is connected to the lower leg member.

Various kinds of lower leg members, foot members, swing phase control devices, stand phase securing devices, etc. having different characteristics which must be adapted to the requirements of the thigh amputated person and secondly having different prices are available for such kinds of prosthesis. The anatomical conditions of various persons are different and a prosthesis for a thigh-amputated person must therefore be additionally adapted to the corresponding anatomical conditions. For a purpose of selecting the various members of such a prosthesis and adapting to the requirements and the anatomical conditions of the thigh amputated person it is necessary to test various combinations of the possible members and their adaptation to the anatomical conditions of the thigh amputated person.

This causes for example the problem that the various swing phase control devices and/or stand phase securing devices have different overall sizes and/or connection possibilities and connection requirements, that the various lower leg members and feet are formed in very different manner just because of their different characteristics and that the replacement of various components of a prosthesis is therefore often impossible or requires a high expense. Thus, the selection of the correct prosthesis including the necessary testing of the various components is very difficult and expensive.

It is the object of the present invention to provide a test prosthesis which allows a combination of various components of a prosthesis in an easy manner.

This object is achieved by a test prosthesis having a thigh member (6), a lower leg member (7), a joint (4) connecting both members, and a knee part (1), characterized in that the knee part is connected to the thigh member or to the lower leg member, respectively, through a connection unit (8) allowing connection of the thigh member with a relative movement between the connected members in a direction inclined with respect to the leg axis.

Further embodiments of the invention are defined in the subclaims.

The design of a knee member according to an embodiment allows a replacement of the swing phase control device which does not effect the respective other components connected to the knee member. Hence, the exchange necessary for selecting the correct swing phase control device is easily possible. Further, the lower leg member can be connected to the foot member or the thigh member can be connected to the knee part or with the lower or upper knee member, respectively, without effecting the respective other components. This also results in an easy exchange of the corresponding members in a manner independent of the other members used in the test prosthesis. The adjustment device of the connection unit allows an adjustment of the position of the thigh member relative to the upper knee member and thus an adjustment of the position of the thigh member relative to the other members used if required by the exchange of the other members.

Further features and advantages of the invention will be apparent from the description of embodiments with reference to the figures. In the figures.

Figure 1:
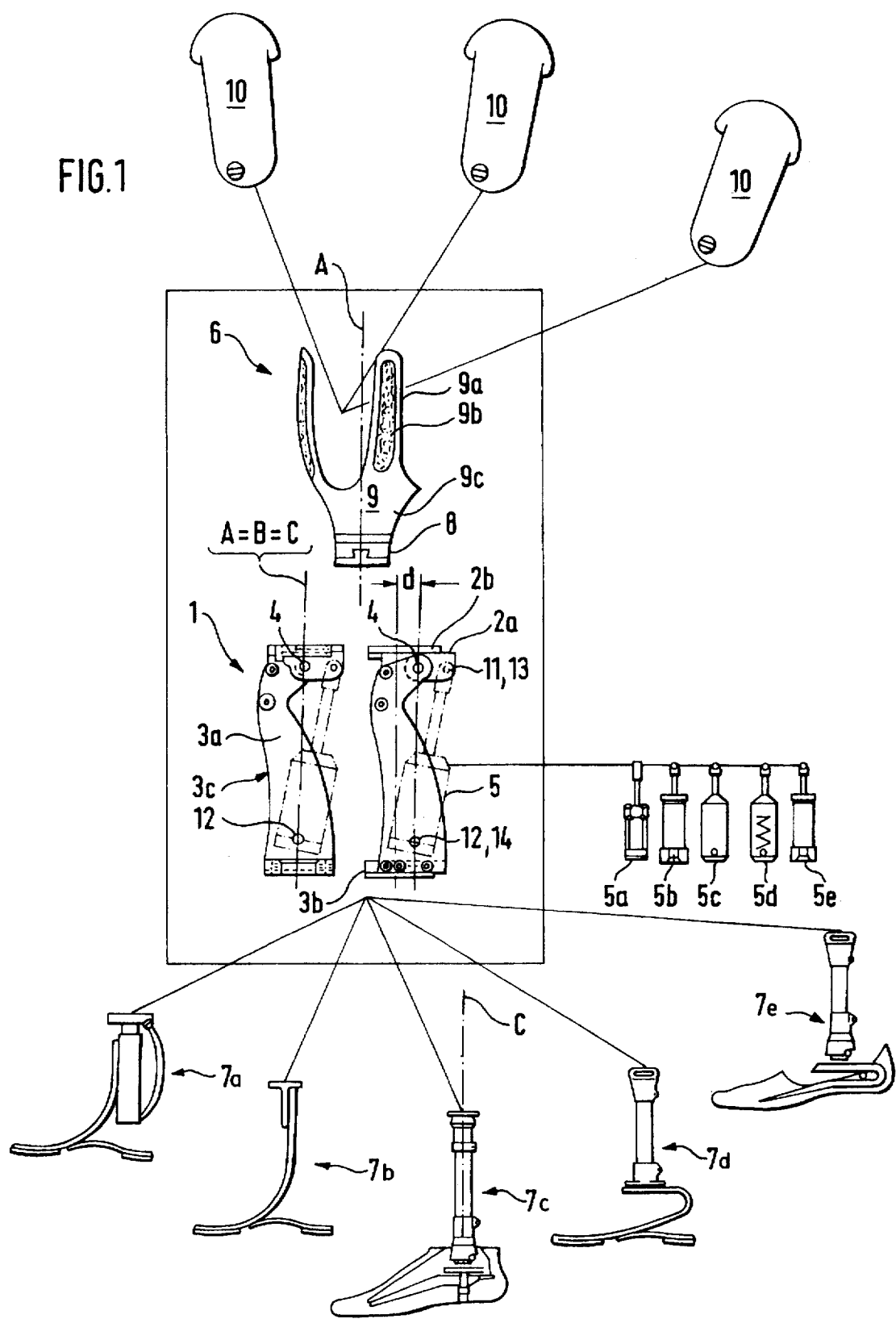
FIG. 1 is a schematical representation of various members of the test prosthesis.

FIG. 1 shows various members according to one embodiment for combination in a test prosthesis. A knee part 1 comprises an upper knee member 2a, 2b and a lower knee member 3a, 3b and a joint 4. The upper knee member comprises a connection member 2a having a first abutment or link point 11 and a slide guide with a slide 2b which can be displaced along the slide guide and adjustably locked therein together with the connection member 2a. The lower knee member comprises two side members 3a which are connected with each other through corresponding connections and, at their bottom ends, by a part having a slide guide, to form a frame. The slide 3b is connected with this frame 3c through the slide guide in a displaceable and adjustably lockable manner. The frame 3c comprises a second abutment or second link point 12. A swing phase control device 5 formed as a piston-cylinder-device can be connected to the first link point 11 of the connection member 3a through its piston rod having a first link part 13. The swing phase control device 5 has a cylinder end with a second link part 14 which is connectable to the second link point 12 of the frame 3c. In the embodiment shown in FIG. 1 the link parts 11, 12, 13, 14 are formed as through bores so that the corresponding first link parts 11, 13 and the corresponding second link parts 12, 14 can be connected through bolts or the like. Thus, various kinds of swing phase control devices and/or stand phase securing devices 5a, 5e can be easily placed into the knee part 1 to form a swing phase control device 5. The devices can be servopneumatical, servohydraulic, mechanical or similar piston cylinder devices or other swing phase control devices or stand phase securing devices.

A thigh shaft connection member 9 having three schematically represented thigh shafts 10 is shown in the upper part of FIG. 1. The thigh shaft connection member can be formed of plastic material or the like and comprises, in the embodiment shown, three upwards pointing fingers 9a joining at a cone-shaped lower portion 9c. Only two of the fingers are shown in FIG. 1. The cone-shaped lower portion of the thigh shaft connection member 9 is connected to a connection unit 8. The connection unit 8 is exchangeable and described further below. The thigh shaft connection member is connected to the upper knee member, in particular with the slide 2b, through the connection unit 8. The upwards pointing fingers 2a of the thigh shaft connection member 9 have respective Velcro fastening bands 9b provided at their inner sides. These fastening bands are schematically indicated in FIG. 1. A thigh shaft 10 having corresponding Velcro Fastening bands provided at its outer surface for cooperation with the above-mentioned fastening bands is inserted between the upwardly pointing fingers of the thigh part connection member 9 and then fixed and held by an adhesive tape bound or placed around the fingers of the thigh shaft connection member.

Five different lower leg members 7a–7e with foot members (lower leg-foot members) are shown in the lower part of FIG. 1. These lower leg members 7 are selectively connected to the slide 3b of the lower knee member 3 for testing or selection.

It is evident from the above explanation that each of the members, i.e. the swing phase-control device, the thigh member or the lower leg member, can be exchanged separately and independently.

Figure 2:
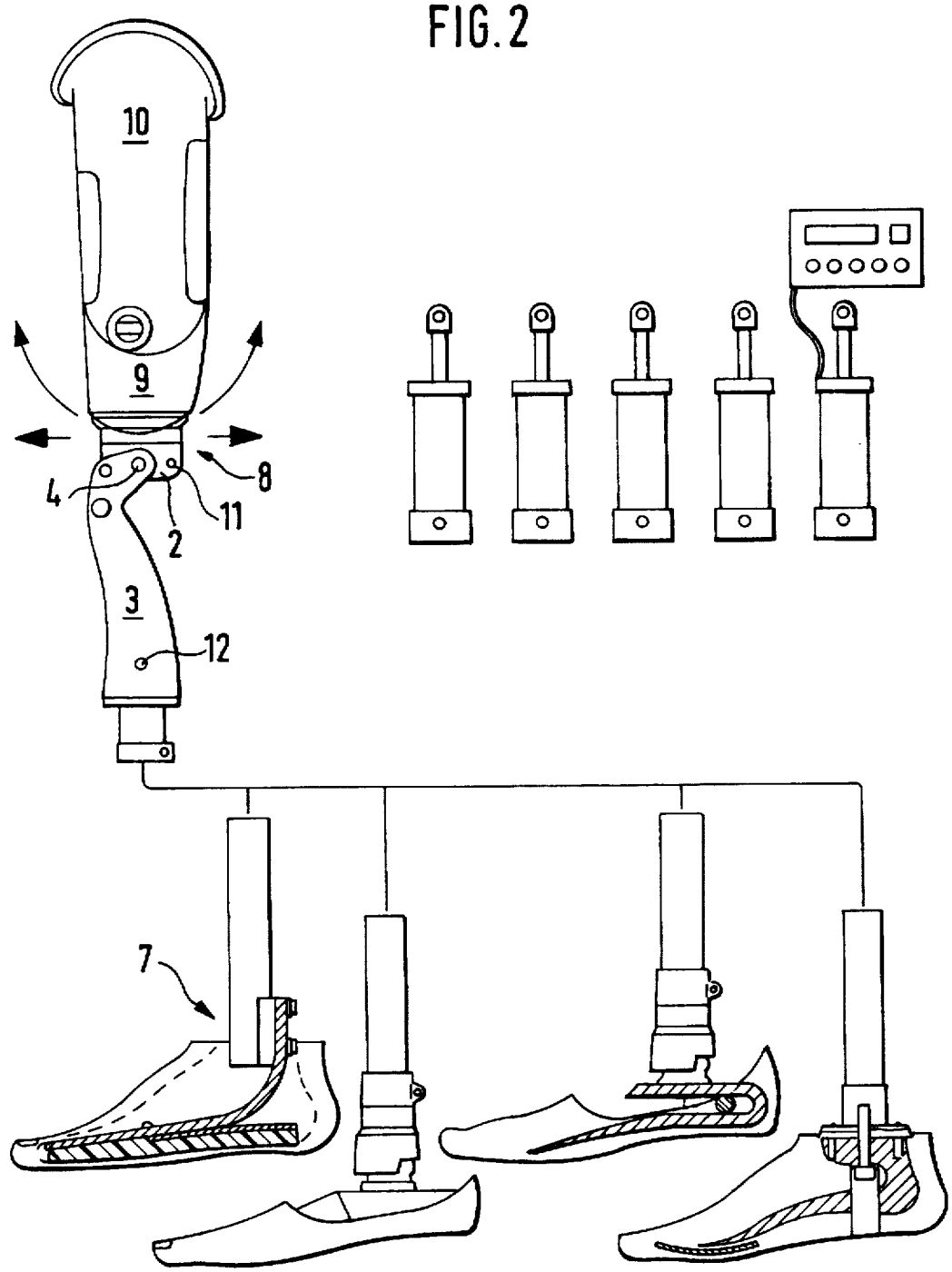
FIG. 2 is a different representation of various members of a second embodiment of the test prosthesis.

It is clearly shown in FIG. 1 that the lower leg members 7a–7e differ from each other in a partially considerable manner. The lower leg members and the foot members are selected for example according to the degree of activity of the amputated person, which results in considerably different requirements to the prosthesis when used for example for an athlete or a rather inactive elderly person. Four lower leg members 7 each having a tubular shape are shown in FIG. 2. If the lower leg members differ only with respect to the various foot members connected thereto, then a flange as schematically shown in FIG. 2 can be used to obtain an even simpler and faster connection with the knee part.

The connection unit 8 shown in the FIGS. 1 and 2 has an adjustment device. This adjustment device serves the purpose of changing the position of the thigh member comprising the thigh shaft connection member and the thigh shaft 10 relative to the upper knee member 2. This means that the thigh member 6 can move relative to the axis of the leg (leg-axis) which is formed by a virtual line through the lower leg member, the knee part and the thigh member. In FIG. 2 a displacement in a plane parallel to the axis of the joint 4 and in a direction perpendicular thereto and a pivot motion in a plane perpendicular to the axis of the joint 4, i.e. in corresponding directions inclined with respect to the leg-axis, are schematically indicated by arrows.

Figure 3:
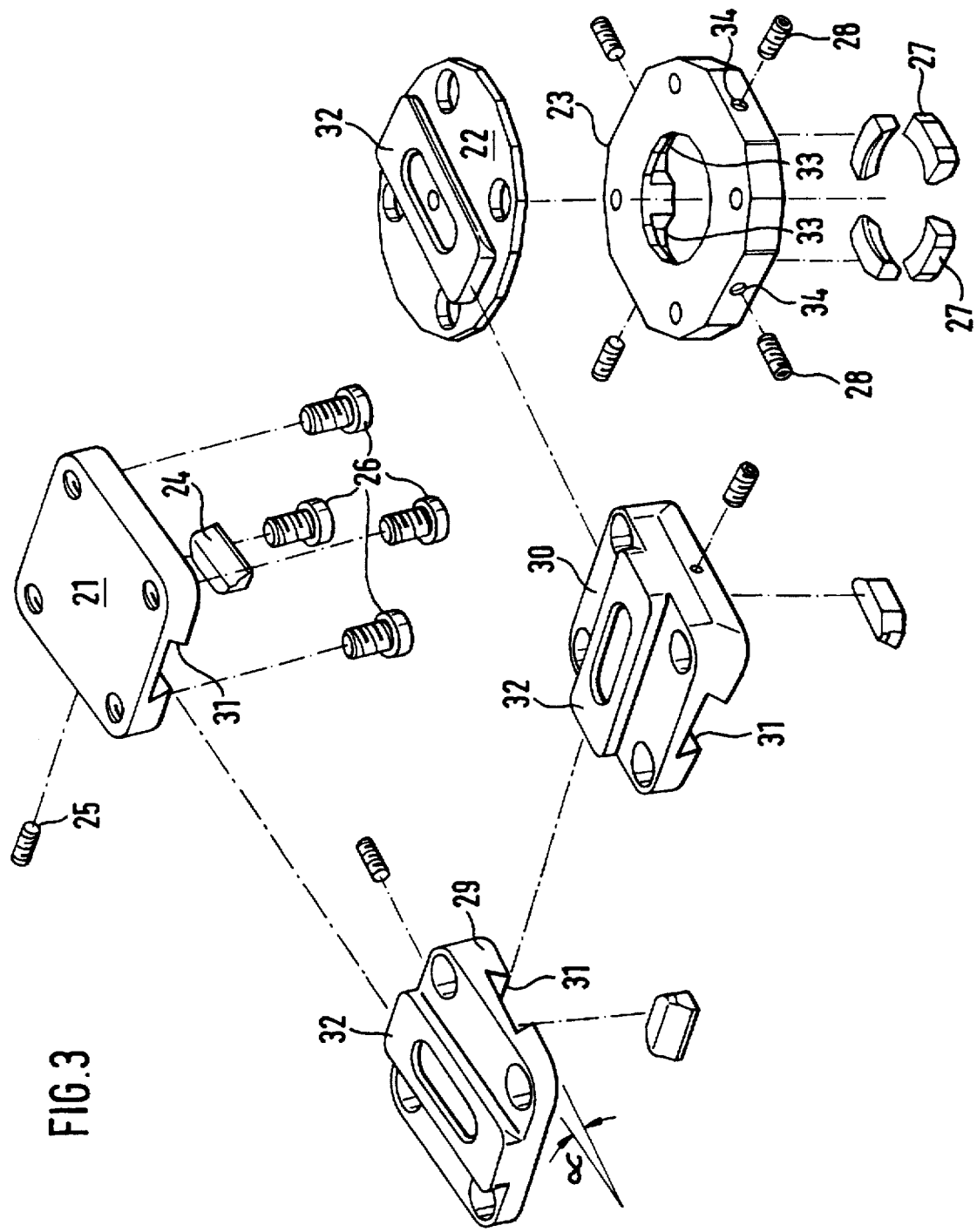
FIG. 3 is an exploded representation of an embodiment of the adjustment device.

FIG. 3 shows an embodiment of such an adjustment device in exploded representation. FIG. 3 shows a first slide member 21, a second slide member 22 and a pivot bearing member 23 of a connection device. The first slide member 21 is plate-shaped with a plane upper surface and a plane lower surface having a slide guide groove 31 with a substantially trapezoidal cross-section. The trapezoidal slide guide groove 31 is formed so that the longer side of the trapezoid is directed to the upper side. The second slide member 22 is also substantially plate-shaped and has a plane lower side and a substantially plane upper side with a projecting slide projection 32 having a cross-section corresponding to the slide guide groove 31. The trapezoidal cross-section of the slide projection 32 is adapted to the trapezoidal cross-section of the slide guide groove 31 to allow an insertion of the slide projection into the slide guide groove 31 and a displacement thereof so that the lower side of the first slide member 21 can be displaced in a plane with respect to the upper side of the second slide member 22. The lower side of the first slide member has a recess therein which is formed to receive a clamping key 24 in this recess. A threaded bore is formed in the first slide member 21 parallel to the upper side thereof to extend into the recess for the clamping key 24. A bolt 25 is inserted into the threaded bore to push the clamping key 24 placed within the recess into the slide guide groove 31 by rotating the bolt. In this manner the position of the first slide member 21 and of the second slide member 22 can be fixed by rotation of the bolt 25 in the threaded bore and corresponding clamping action of the clamping key 24. The first slide member 21, the second slide member 22, the clamping key 24 and the bolt 25 thereby form an adjustment device which allows a one-directional displacement in a plane parallel to the upper side and lower side of the slide members 21, 22.

In the embodiment shown in FIG. 3 the first slide member 21 forms the upper part of the connection unit 8. The thigh shaft connection member 9 is connected to the first slide member 21 through the bolts 26 shown in FIG. 3. The second slide member 22 is connected to the pivot bearing member 23 through not shown fastening members. The pivot bearing member 23 is substantially plate-shaped and has a substantially circular hole in its center. Four recesses 33 are symmetrically arranged within the circular hole. Corresponding clamping keys 27 can be inserted into these recesses 33. The clamping keys 27 can be displaced in direction to the interior of the hole of the pivot bearing member 23 by bolts 28 inserted into a threaded bore 34, in a manner analogous to the displacement of the clamping key 24 through the bolt 25. The pivot bearing member 23 has its hole placed onto a (not shown) pivot pin which forms a first portion of the connection unit 8 and is fastened to the upper knee member 2. The pivot bearing member 23 forming a second part of the connection unit 8 can be rotated around the axis of the pivot pin and the position of the pivot bearing member 23 relative to the pivot pin, and therefore relative to the upper knee member 2, is fixed by tightening the bolts 28 in the threaded bores 34.

The first and second slide members 21, 22, the pivot bearing member 23, the clamping keys 24, 27 and the bolts 25, 28 thereby form a connection unit having an adjustment device allowing an adjustment of the position of the thigh member 6 relative to the upper knee member 2 with two degrees of freedom, namely a displacement of the slide and a rotation of the pivot bearing member around the pivot pin.

FIG. 3 further shows a third slide member 29 and a fourth slide member 30. These slide members are substantially wedge-shaped, i.e. their substantially plane upper and lower sides are not parallel but includes an angle A which is preferably in the range of 0–10 degrees. The third and fourth slide member 29, 30 both have a slide projection 32 formed at their upper side and a slide guide groove 31 formed at their lower sides, corresponding to the projections 32 and grooves 31 of the first and second slide members 21, 22. If the wedge-shaped slide members are placed between the first slide member 21 and the second slide member 22, their use provides for further degrees of freedom of displacement and by selecting the angle a of the wedge, for an additional inclination of the first slide member 21 with respect to the second slide member 22. As a consequence, the thigh member 6 is also inclined with respect to the upper knee member 2. This inclination can be adjusted by selecting different angles a for the wedges. Thus, in the embodiment shown in FIG. 2 the indicated pivoting movement and a change of the inclination of the thigh member with respect to the upper knee member is possible.

Alternatively, similar slide members with groove and projection having a parallel upper end lower sides, i.e. no relative angle therebetween, can be used in place of the third and/or fourth wedge-shaped slide members 29, 30.

With reference to FIG. 1 a further feature of the embodiment of the test prosthesis shown in FIG. 1 will be described. A swing phase control device 5 not necessarily comprises a stand phase securing device, i.e. a lock against buckling of the prosthesis in standing state. This means that the axially aligned composition of a test prosthesis depends on the use of a swing phase control device with or without stand phase securing device. The axially aligned composition means that in a swing phase control device with stand phase securing device the longitudinal axis A of the thigh member, the longitudinal axis B of the knee part defined by the axis of the joint 4 and the lower link point 12, and the longitudinal axis C of the lower leg member 7 are aligned, as shown in the left-hand representation of the knee part in FIG. 1, or that the footpoint of the axis A on the upper knee member 2 is at least on the axis B.

If the swing phase control device has no stand phase securing device, the above aligned arrangement would result in an instable equilibrium and a secure stand of the thigh amputated person therefore requires that the longitudinal axis B of the knee part, i.e. the line extending through the pivot axis of the joint 4 and the link point 12, is displaced backwards by a distance d with respect to the footpoints of the axis A, B of the thigh member and the lower leg member on the upper and lower knee members 2, 3, respectively. This state is indicated in the right-hand representation of the knee part in FIG. 1.

This displacement possibility for obtaining an axially correct arrangement dependent on the use of a swing phase control device with or without stand securing device, is obtained by using the slides 2b, 3b of the upper knee member and of the lower knee member 2, 3.

I claim:

1. A leg prosthesis comprising a thigh member;

a lower leg member;

a knee part having an upper knee member, a lower knee member and a joint connecting said knee members;

said thigh member, lower leg member and knee part being positioned along a leg axis, a swing phase control device having a first end and a second end, said first end being connected to said upper knee member and said second end being connected to said lower knee member; and a connection unit comprising first means for connecting said thigh member to said upper knee member and second means for connecting said lower leg member to said lower knee member, each of said first and second means comprising means for providing a relative displacement of the respective connected members in a direction other than said leg axis, said second means comprising quick exchange means.

2. The leg prosthesis of claim 1, wherein said thigh member comprises a thigh connection member and a thigh shaft.

3. The test leg prosthesis of claim 1, wherein said connection unit comprises a slide having a first slide member, a second slide member, means for allowing a relative displacement of said first slide member and said second slide member and means for locking said first and second slide members in a relative position.

4. The leg prosthesis of claim 3, wherein said slide comprises a compound slide having a third slide member arranged between said first slide member and said second slide member, and means for displacing and locking said third slide member in a first direction and in a first plane with regard to said first slide member and for displacing and locking said third slide member in a second direction in a second plane relative to said second slide member.

5. The leg prosthesis of claim 4, wherein said first slide member, said second slide member or said third slide member comprises an upper side inclined relative to a lower side thereof.

6. The leg prosthesis of claim 1, wherein said connection unit comprises a first member, a second member and means for pivoting said second member with respect to said first member around an axis which is substantially parallel to said leg axis.

7. The leg prosthesis of claim 1, wherein said knee part comprises a frame.

8. The leg prosthesis of claim 7, wherein said swing phase control device comprises piston-cylinder means and a first and second link point for replaceably connecting said piston-cylinder means to said knee part.

9. The leg prosthesis of claim 8, further comprising means for displacing said first or second link point relative to said frame in a direction other than said leg axis.

10. The leg prosthesis of claim 1, wherein said lower leg member comprises one of a plurality of different lower leg-foot members.

11. The leg prosthesis of claim 1, further comprising a set of exchangeable swing phase control devices, said set including at least one servopneumatic, one servohydraulic and one mechanical device.

12. The leg prosthesis of claim 1, wherein said swing phase control device comprises piston-cylinder means and a first and second link point for replaceably connecting said piston-cylinder means to said knee part.

* * * * *